United States Patent [19]
Craig et al.

[11] Patent Number: 4,852,738
[45] Date of Patent: Aug. 1, 1989

[54] DISPOSABLE DENTAL TRAY

[75] Inventors: Richard Craig, Joliet; Brian L. Wilt, Frankfort, both of Ill.

[73] Assignee: HealthPak, Incorporated, Joliet, Ill.

[21] Appl. No.: 243,417

[22] Filed: Sep. 12, 1988

[51] Int. Cl.$^4$ ............................ A61C 3/00; B65D 1/36
[52] U.S. Cl. .................................... 206/369; 206/63.5; 206/519; 206/558; 206/561; 206/564; 220/1 S; 220/22
[58] Field of Search ............................ 220/20, 22, 1 S; 206/368, 369, 63.5, 519, 561, 564, 507, 558

[56] References Cited

U.S. PATENT DOCUMENTS

| | | | |
|---|---|---|---|
| 857,240 | 6/1907 | Henning | 206/369 |
| 2,491,771 | 12/1949 | Roos | 206/369 |
| 3,442,376 | 5/1969 | McDivit | 206/63.5 |
| 3,804,239 | 4/1974 | O'Brien | 206/558 |
| 3,890,096 | 6/1975 | Nichol et al. | 206/369 X |
| 3,982,630 | 9/1976 | Garnier | 206/369 |
| 4,256,457 | 3/1981 | Behring | 206/369 X |
| 4,353,694 | 10/1982 | Pelerin | 206/369 X |
| 4,483,443 | 11/1984 | Caille | 206/564 X |

Primary Examiner—John Rivell
Attorney, Agent, or Firm—Polster, Polster & Lucchesi

[57] ABSTRACT

A disposable dental tray includes a disposable tray body defining four utility compartments. Three of the utility compartments are disposed along a first side of the tray body, the fourth utility compartment being disposed along a second side of the tray body. All four of the utility compartments have relatively flat bases and are defined by integrally formed ridges extending upwardly from the compartment bases. Each compartment is surrounded by a defining ridge, interior defining ridges being offset from each other so that no interior ridge extends completely across the tray. The tray body further includes an instrument compartment defined by an encircling ridge extending upwardly from the base of the instrument compartment. The instrument compartment has integrally formed therein a series of grooves for holding dental instruments, which grooves are elevated above the base of the instrument compartment. An integrally formed reinforcing member extends across the instrument compartment in generally the same direction as the instrument holding grooves without interfacing with the usability of any of the grooves.

10 Claims, 3 Drawing Sheets

DISPOSABLE DENTAL TRAY

BACKGROUND OF THE INVENTION

This invention relates to dental equipment and more particularly to dental trays which prevent the spread of disease.

Various dental procedures involve the use of a dental tray for holding in a readily accessible manner the dental instruments and other accessories needed to perform that procedure. These trays are generally standardized in terms of size, overall shape, and general placement of the compartments formed therein. Heretofore, these dental trays have been injection molded from a hard plastic such as polypropylene.

The prior art polypropylene trays have served their function well for many years, but they could be improved. One area in which improvement could be achieved is in the area of infection control and cross contamination. The prior art polypropylene trays are reusable trays which must be thoroughly cleaned between uses to prevent the spread of disease (such as serum hepatitis, acquired immune deficiency syndrome (AIDS), or the like) between successive patients or between the patient and a dental professional (hygienist, dental assistant, or dentist). Moreover, the cleaning operation itself exposes the dental professional to the risk of infection from the blood present on the tray.

Since the adequacy of the cleaning operation with the prior art trays often depends upon the amount of time available to perform the cleaning and the conscientiousness of the person performing the cleaning operation, the prior art trays were not always adequately cleaned.

In addition to the possibility of transmitting diseases with the prior art trays, the cleaning operation itself added to the expense of the dental procedure because of the time and materials required to perform the cleaning operation properly.

Because of the fact that the prior art tray is commonly used, however, it is not desirable to greatly change the overall appearance of the tray in designing a replacement. Any replacement tray should be immediately useable by the dental professional without extensive training on the use of the replacement tray.

SUMMARY OF THE INVENTION

Among the various objects and features of the present invention may be noted the provision of a dental tray which eliminates, when used properly, the possibility of disease being transmitted by the tray from one patient to another.

Another object is the provision of such a dental tray which greatly reduces the possibility of disease being transmitted by the tray from a patient to a dental professional during the cleaning operation by eliminating the cleaning operation.

A third object is the provision of such a dental tray which is economical to use.

A fourth object is the provision of such a dental tray which is disposable.

A fifth object is the provision of such a dental tray which is also very similar to the standard dental tray so that it may readily be used as a replacement tray by the dental professional.

A sixth object is the provision of such a dental tray which has maximized structural strength for a tray made of thermoformed plastic or of some other disposable product.

Other objects and features will be in part apparent and in part pointed out hereinafter.

Briefly, a disposable dental tray of the present invention includes a disposable, unitary tray body defining four utility compartments. The tray body is generally rectangular and is sized to accept a plurality of dental instruments and accessories. Three of the utility compartments are disposed along a first side of the tray body with a first of the compartments being disposed in a corner of the tray body. The fourth utility compartment is disposed adjacent the first compartment along a second side of the tray body. At least one of the three compartments disposed along the first side has a width as measured from the first side different from the width of at least one of the other of those three compartments. All four of the utility compartments have relatively flat bases and are defined by integrally formed ridges extending upwardly from the compartment bases. Each compartment is surrounded by a defining ridge. The width of the first compartment as measured from the second side is different from the width of the fourth utility compartment as measured from the second side.

BRIEF DESCRIPTION OF THE DRAWINGS

In the drawings.

Similar reference characters indicate similar parts throughout the several views of the drawings.

DESCRIPTION OF THE EMBODIMENT

Figure 1:
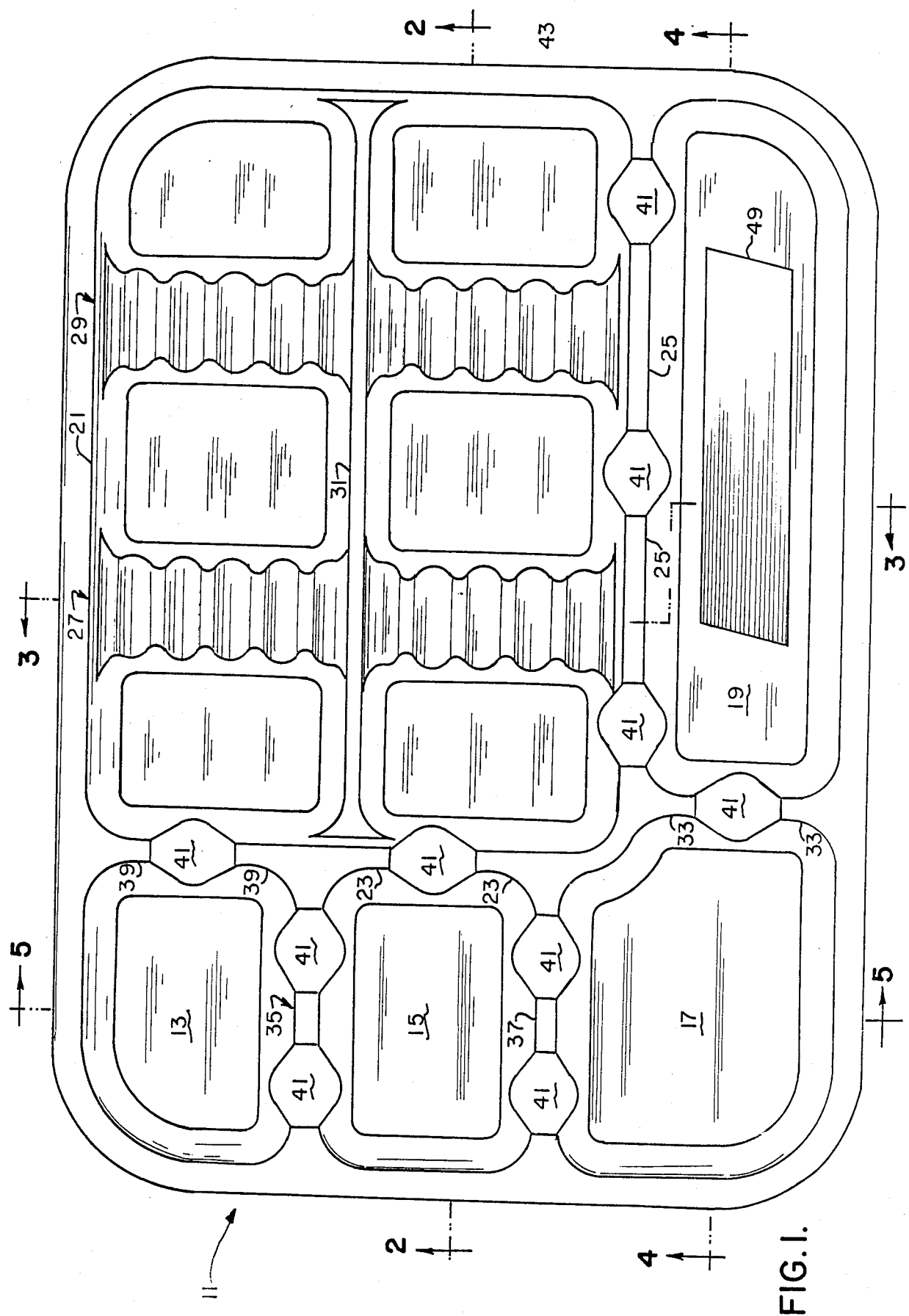
FIG. 1 is a top plan of a disposable dental tray of the present invention.

Referring now to the drawings, a disposable dental tray 11 of the present invention is a unitary tray injection molded from a suitable plastic foam such as polystyrene. Polystyrene foam is selected for the material of tray 11 for purposes of cost, since it results in a tray which is inexpensive enough to be disposed of after a single use. Alternatively, such a tray could be formed of a disposable paper material, polyethylene, other foam or laminated foam thermoformed plastics, or any other commodity-type material which provides the necessary strength at low cost.

Tray 11 has formed therein four utility compartments 13, 15, 17 and 19 which are similar to but not identical with the compartments of the standard dental tray which tray 11 replaces. In addition to compartments 13 through 19, tray 11 also includes an instrument compartment 21 for holding various dental instruments during a dental procedure.

As can be seen from FIGS. 2 through 5, the various compartments of tray 11 are separated by reinforcing ridges which define and separate the compartments while supplying rigidity to the tray as a whole. For example, compartments 15 and 21 (FIG. 2) are separated by a ridge 23. This ridge, like all the ridges, is hollow to reduce the weight and material required for tray 11.

Figure 3:
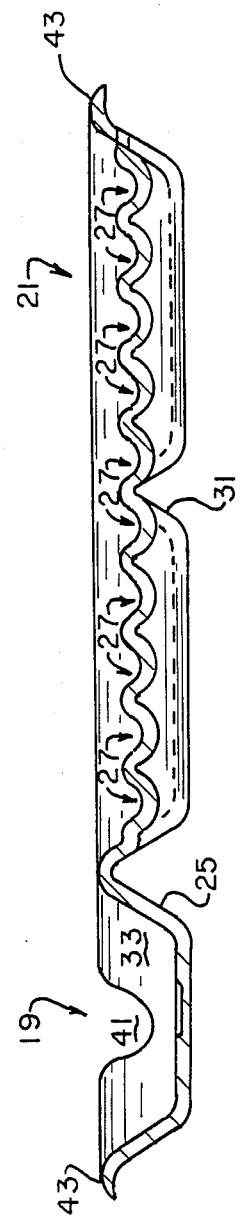
FIG. 3 is a sectional view taken along line 3—3 of FIG. 1.
Figure 2:
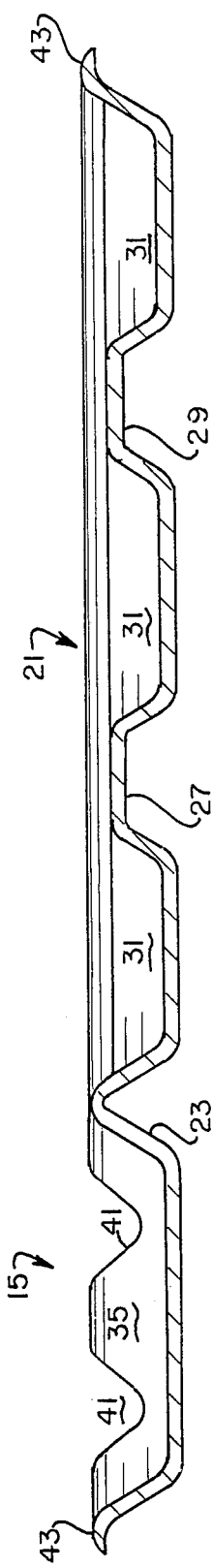
FIG. 2 is a sectional view taken along line 2—2 of FIG. 1.

Similarly, compartment 19 is separated from instrument compartment 21 by a ridge 25 (FIG. 3). It should also be noted from FIG. 3 that compartment 21 has formed therein a series of parallel grooves 27 to hold the dental instruments in place. As can be seen from FIG. 1, grooves 27 are one of a set of two series of grooves 27 and 29 which are disposed above the floor or base of compartment 21 to hold said dental instruments in place.

A reinforcing ridge 31 (FIGS. 1 and 3) runs across compartment 21 to provide additional support. This ridge, however, has a lower profile than the ridges heretofore described as separating various compartments. In fact, the profile of ridge 31 and its placement is such that it does not interfere with any of the grooves 27 or 29. That is, ridge 31 provides support without in any way interfering with the function of compartment 21.

Figure 4:
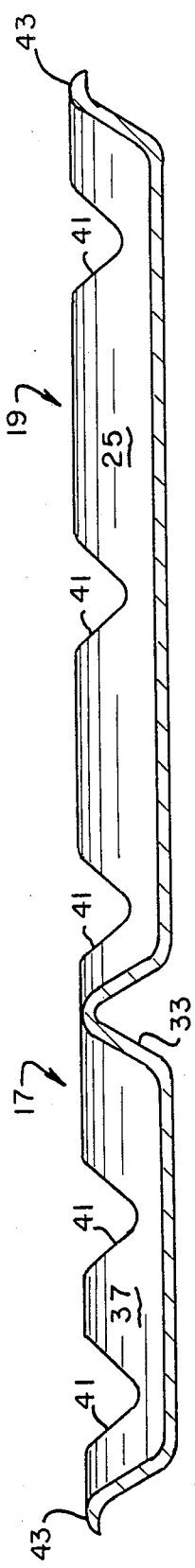
FIG. 4 is a sectional view taken along line 4—4 of FIG. 1.
Figure 5:
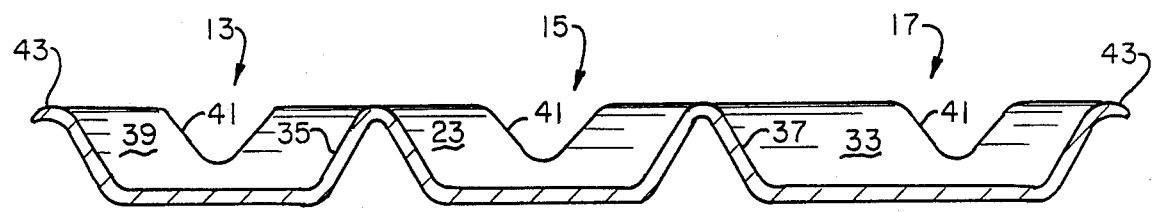
FIG. 5 is a sectional view taken along line 5—5 of FIG. 1.

Referring to FIGS. 4 and 5, a ridge 33 separates compartments 17 and 19, a ridge 35 separates compartments 13 and 15, and a ridge 37 separates compartments 15 and 17. As can also be seen from FIG. 1, compartment 13 is separated from instrument compartment 21 by a ridge 39.

An examination of FIGS. 1 through 5 reveals that all the compartment separating and defining ridges are interrupted by cylindrical focus points 41. For clarity, those figures have been simplified to remove a line crossing the tops of these focus points in the drawings. That line, if present, would represent the rim or lip 43 of the tray which extends around the periphery of the tray.

Figure 6:
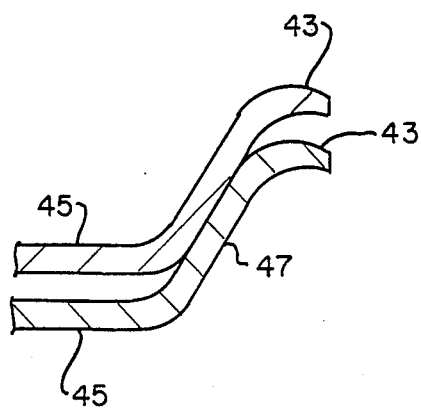
FIG. 6 is a sectional view of the edge of the tray of FIG. 1 illustrating the nestability feature of said tray.

The edge of tray 11 is illustrated in more detail in FIG. 6. Each side of the tray extends upwardly from the base 45 of the tray with an angled portion 47 which provides a suitable draft so that a plurality of trays 11 may be nested together for shipping and storage as shown. It should be noted that angled portion 47 functions like the ridges in that it defines one or more sides of the various compartments. The tray terminates on all sides in lip 43, which extends outwardly and somewhat downwardly as shown.

Figure 7:
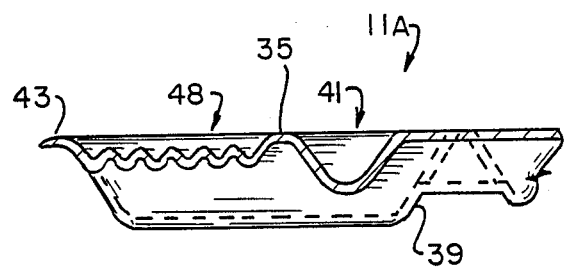
FIG. 7 is a sectional view of one corner of the tray illustrating an alternative construction.

It may be desired to also provide in dental tray 11 a holder for the burrs used by the dentist during certain dental procedures. For this purpose a burr holder 48 consisting of six parallel grooves is integrally formed in the ridge 35 disposed between compartments 13 and 15. More specifically, the burr holder takes the place of the leftmost focus point 41 shown in FIG. 1 in ridge 35. Tray 11 in FIG. 7 is labelled 11A to signify this difference in construction.

Turning back to FIG. 1, fourth utility compartment 19 also includes a recess 49 in which a company name (for example) may be imprinted or molded.

As can be readily observed from FIG. 1, the first three utility compartments are disposed on one side of generally rectangular tray 11. Note, however, that the widths of compartments 13 and 15 as measured from that side differ somewhat from the width of compartment 17. This is because ridges 23 and 39 are not aligned with ridge 33. As a result of this offset in the ridges, there is not a hinge point across tray 11 in this direction along which the tray can bend and fail.

Similarly, compartments 17 and 19 are disposed along a second side of the tray, but the widths of these two compartments as measured from that second side also differ. This is accomplished by offsetting ridges 25 and 37, again to prevent the formation of a hinge point in that direction across the tray.

In like manner, ridge 31 through the instrument compartment 21 is offset from ridge 35 between compartments 13 and 15 to prevent the formation of a hinge point there.

Inspection of FIG. 1 reveals no ridge which extends in a straight line across tray 11. As a result the ridges provide the desired support and define the compartments without providing a point for failure of the tray.

In view of the above it will be seen that the various objects and features of the present invention are achieved and other advantageous results obtained. Various modifications of the embodiment of the present invention shown and described herein are intended to be covered by the present application, the scope of the invention being limited only by the appended claims.

Having thus described the invention, what is claimed and desired to be secured by Letters Patent is:

1. A disposable dental tray comprising a disposable, unitary tray body defining four utility compartments, said tray body being generally rectangular and being sized to accept a plurality of dental instruments and accessories, three of said utility compartments being disposed along a first side of the tray body with a first of said compartments being disposed in a corner of the tray body, the fourth utility compartment being disposed adjacent the first compartment along a second side of the tray body, at least one of the three compartments disposed along the first side having a width as measured from the first side different from the width of at least one of the other of said three compartments, all four of said compartments having relatively flat bases and being defined by integrally formed ridges extending upwardly from the compartment bases, each compartment being surrounded by a defining ridge, the width of the first compartment as measured from the second side being different from the width of the fourth utility compartment as measured from the second side.

2. The disposable dental tray as set forth in claim 1 wherein the tray body consists essentially of molded polystyrene foam.

3. The disposable dental tray as set forth in claim 1 wherein at least some of the defining ridges have generally cylindrical focus points formed therein.

4. The disposable dental tray as set forth in claim 1 wherein the tray body further includes an instrument compartment defined by an encircling ridge extending upwardly from the base of the instrument compartment.

5. The disposable dental tray as set forth in claim 4 wherein the instrument compartment is disposed adjacent the fourth utility compartment on one side and adjacent at least some of the first three utility compartments on another side, the interior defining ridges for the utility compartments being offset from the interior defining ridges of the instrument compartment so that no single defining ridge extends completely across the interior of the tray.

6. The disposable dental tray as set forth in claim 4 wherein the instrument compartment has integrally formed therein a series of grooves for holding dental instruments, said grooves being elevated above the base of the instrument compartment.

7. The disposable dental tray as set forth in claim 6 further including an integrally formed reinforcing member extending across the instrument compartment in generally the same direction as the instrument holding grooves.

8. The disposable dental tray as set forth in claim 7 wherein the integrally formed reinforcing member has a profile no higher than the profile of the instrument holding grooves so as to not interfere with the usability of any of the grooves.

9. The disposable dental tray as set forth in claim 1 wherein the tray body has an outwardly and somewhat downwardly extending lip formed therein around the periphery of the tray body.

10. The disposable dental tray as set forth in claim 1 wherein the tray body has formed in at least one of the compartment defining ridges a holder for a plurality of dental instruments such as dental burrs.

* * * * *